United States Patent
Simone

(10) Patent No.: US 7,319,970 B1
(45) Date of Patent: Jan. 15, 2008

(54) METHOD AND APPARATUS FOR LIFESTYLE RISK EVALUATION AND INSURABILITY DETERMINATION

(76) Inventor: Charles B. Simone, 123 Franklin Corner Rd., Lawrenceville, NJ (US) 08646

( * ) Notice: Subject to any disclaimer, the term of this patent is extended or adjusted under 35 U.S.C. 154(b) by 0 days.

(21) Appl. No.: 08/605,628

(22) Filed: Feb. 22, 1996

Related U.S. Application Data

(63) Continuation of application No. 08/530,729, filed on Sep. 19, 1995, now abandoned, which is a continuation of application No. 08/063,734, filed on May 20, 1993, now abandoned.

(51) Int. Cl.
  *G06Q 40/00* (2006.01)
  *G06F 19/00* (2006.01)
  *G09B 23/28* (2006.01)

(52) U.S. Cl. .............. 705/4; 705/3; 434/262
(58) Field of Classification Search ........ 364/401, 364/408, 400, 406, 401 R; 395/925; 705/1, 705/2, 3, 4, 30, 35
See application file for complete search history.

(56) References Cited

U.S. PATENT DOCUMENTS

| | | | |
|---|---|---|---|
| 4,722,055 A | 1/1988 | Roberts | 364/408 |
| 4,750,121 A | 6/1988 | Halley et al. | 364/408 |
| 4,752,877 A * | 6/1988 | Roberts et al. | 364/408 |
| 4,766,539 A | 8/1988 | Fox | 364/401 |
| 4,831,526 A | 5/1989 | Luchs et al. | 364/401 |
| 4,837,693 A | 6/1989 | Schotz | 364/408 |
| 4,839,804 A * | 6/1989 | Roberts et al. | 364/408 |
| 4,975,840 A * | 12/1990 | DeTore et al. | 364/401 |
| 5,084,819 A * | 1/1992 | Dewey et al. | 434/262 |
| 5,301,105 A * | 4/1994 | Cummings, Jr. | 364/401 |
| 5,325,291 A * | 6/1994 | Garrett et al. | 705/4 |
| 5,712,984 A * | 1/1998 | Hammond et al. | 705/4 |

FOREIGN PATENT DOCUMENTS

JP 11242711 A * 9/1999

OTHER PUBLICATIONS

"National Underwriter: Proper & Casualty/Risk & Benefits Mngt." Feb. 1991 by Haggerty, Alfred.*
"National Underwriter: Property/Casualty", May 2, 1986. Journal Code : NUPC.*
McDonnell, Lynda; "Paying for Health Eager to Control Health-Care Costs, More Companies . . . ," May 3, 1992, St. Paul Pioneer Dispatch, p. 1G (4 pages).*
Lynch, Catherine; "Stay Healthy: Pay Le$$ for Health Insurance," Nov. 1992, Life & Health Insurance Sales, vol. 135 No. 11, pp. 20-22 (4 pages).*

* cited by examiner

*Primary Examiner*—C. Luke Gilligan
*Assistant Examiner*—Rachel L. Porter
(74) *Attorney, Agent, or Firm*—Dickstein Shapiro LLP

(57) ABSTRACT

An automatic health and lifestyle analysis computer system is provided, which surveys individual respondents and provides insurability estimates and cost evaluations based upon answers to the surveys.

9 Claims, 8 Drawing Sheets

US 7,319,970 B1

METHOD AND APPARATUS FOR LIFESTYLE RISK EVALUATION AND INSURABILITY DETERMINATION

This application is a continuation, of application Ser. No. 08/063,734, filed May 20, 1993, now abandoned.

FIELD OF THE INVENTION

The present invention involves a computer system which evaluates risk factors to determine costs to an employer or administrator of a health insurance program based on the evaluated life factors of the individual to be insured. The system evaluates lifestyle factors and identifies those individuals at risk. The system then can assign dollar values to each factor so that an overall risk evaluation and monetary insurance value assessment can be made.

BACKGROUND OF THE INVENTION

Today, a person who is healthy and constantly modifying his or her disease risk factors, is at an unfair disadvantage in the health insurance arena. Because that individual's healthy lifestyle frequently places him or her above the typical person, the high positive health rating effectively subsidizes someone else who goes through life with multiple disease risk factors, and does nothing to modify them. In effect, therefore, the healthy individual is penalized. For the employer, this penalty translates into money. That is, the employer, who encourages its employees to be healthy, will nonetheless be penalized for those who are not. In addition, that employer, when assessing potential future costs for health insurance for a pool of employees, has absolutely no basis to evaluate that pool's collective risks from a health insurance standpoint.

Presently, no systems exist which focus on an average person's health risks and then provide that person with an incentive to modify them. Moreover, no system exists which aids the employer and the insurer in determining insurance costs by providing a financial evaluation that reflects the impact of chosen lifestyles on health insurance premiums. Additionally, existing insurance valuation systems are too narrowly focused on existing diseases and thus fail to account for potential diseases that could likely occur in an individual who has multiple risk factors.

For example, U.S. Pat. No. 4,975,840 to DeTore et al., discloses a risk evaluation system for life insurance where computer software automatically provides evaluation data for policy classification. To accomplish this goal, DeTore et al. relies on an underwriting knowledge database which is addressed by a computer in conjunction with an application database. Both databases store problem issues and assign weights to those issues which result in a subsequent risk classification. The assigned weights, in effect, reflect debits/credits for an insurance policy.

However, DeTore et al. only focus on evaluating existing medical problems. It lacks any capability for assessing lifestyle data. In addition, De Tore et al. does not perform a determination pertinent to health insurance coverage, only to life insurance. Accordingly, the DeTore system fails to effectively assess an individual's "lifestyle" in order to attribute lifestyle factors to insurance valuation. It also fails to provide a basis for determining the effect of lifestyle choices on health insurance coverage.

U.S. Pat. No. 4,831,526 to Luchs et al. addresses the need for a system that automates the task of insurance quotation through a system which prepares and writes insurance contracts based upon data provided from clients. Unlike DeTore et al., Luchs et al. involves automating the entire insurance process, i.e., taking the application form, evaluating the application, and developing an insurance coverage based upon the risk assessments performed by the computer. However, Luchs et al. is solely directed to home insurance evaluation. As a consequence, Luchs et al. fail to address the problem of insuring an individual's health based upon an individual's lifestyle issues. There is no consideration for the factors which affect healthy risks that are unique to an individual's health.

Finally, U.S. Pat. No. 4,837,693 to Schotz relates to a system which enables employers to gather employee information in order to administer and implement a group insurance plan. Schotz relies on a computer system which automatically converts group insurance coverage into individual term contracts. The computer system also allows an insurer to readily underwrite the insurance plan. Schotz includes a database of employee census data which includes, among other things, an employee's name, hiring date, age, birth date, salary, status, and sex. Schotz, however, is solely directed to providing insurance risk adjustments for life insurance. As a consequence, Schotz can not assess an employee's lifestyle or health insurance risk based upon lifestyle choices. In addition, Schotz fails to address the need for a system which is directed to assessing health insurance coverage particularized to the individual risk assessments derived from an individual's lifestyles.

In sum, there are many types of potentially insurable health-related risks that range from cancer, heart disease, medical tests, obesity, environmental sources, etc. Individuals and companies, therefore, desperately need a means by which they can assess these risks and provide a basis for improving both an individual's health, determine his health risks and assess the overall liability of the employer for such health risks.

SUMMARY OF THE INVENTION

In view of the foregoing, it should be apparent that a need exists for a system and method for evaluating the health insurance liabilities of individuals based upon their respective lifestyles. It is, therefore, a primary object of the invention to provide a computer system which assesses health insurance risks based upon inputs reflecting lifestyle choices of an individual respondent to a lifestyle/health survey. The computer system combines survey data with lifestyle weights assigned to specific risk factors in order to evaluate how much should be charged to an employer or administrator of a health insurance program based on the life factors of the insured respondents.

More particularly, it is an object of the invention to evaluate an individual's lifestyle factors and identify those individuals at risk and then assign monetary values and/or weights associated with monetary values for each risk factor.

It is another object of the invention to provide a health insurance computer system wherein the monetary values pertaining to health insurance premiums are automatically set based upon the computerized analysis of the health insurance risks.

It is yet a further object of the invention to provide a computer system which analyzes a variety of lifestyle factors for a tested individual. Such factors include personal data, occupation related data, family history factors, nutrition, exercise and sexual-social behavior.

Another object of the invention is to provide an insurance evaluation computer system in which health information is combined with a wide array of laboratory tests.

Another object of the invention is to provide a computer system for assessing insurance risks by attaching a value to particular survey data which affects an overall insurance amount.

It is yet another object of the invention to provide a computer system which analyzes survey data based on individual health lifestyle factors by attaching points to each response to a plurality of survey answers. When the total number of points tabulated from such data exceed a threshold, insurance premium costs for health insurance are changed based upon that threshold.

It is yet another object of the invention to provide a health insurance evaluation system wherein the entire process is automated so that a potential insured can interactively provide his or his responses to computer generated questions in a computer monitor. The responses to those questions can then be analyzed by an employer or insurance carrier by having the computer system attach positive or negative points to each answer. Negative points are assigned to those answers which signify increased risk and positive points are assigned to answers which indicate decreased risk. When answers exceed predetermined thresholds, then a particular health insurance premium value is effected positively or negatively.

It is yet a further object of the invention to provide a health insurance evaluation and policy determination system wherein at least four levels of health insurance plans are contemplated. A first level is for survey respondents whose scores reflect an overall healthy lifestyle. The second level is for individuals whose scores reflect a moderately healthy lifestyle with several discrete risks. The third level would be for respondents whose results indicate more critical health risks and the fourth level would be for those individuals whose scores indicate an overall unhealthy lifestyle that presents significant risks to an insurer.

It is yet a further object of the invention to provide a health insurance evaluation system in which lifestyle questions are checked with laboratory results in order to make a determination of the relative truth of the respondent's answers.

It is yet a another object of the invention to provide a health assessment system in which past values can be correlated to present health insurance premiums subsequent to the initial evaluation so that an improvement in an individual's health can effectively result in premium rewards (i.e. discounts, extra coverage). The rewards are provided for those individuals who either (1) stay healthy or (2) whose health has improved since the initial survey.

Briefly, these and other objects of the invention are accomplished in its apparatus aspects by means of a computer system which employs an automated interactive survey capability which receives lifestyle data in order to evaluate risk factors associated with that data and determine how much is to be charged to an employer or administrator of a health insurance program based upon that data. Sixteen different categories defining an overall lifestyle are tested. The categories for testing include personal data such as age, sex and whether the respondent uses tobacco. Other lifestyle categories for testing include: occupational risks, nutrition, exercise, social/sexual patterns, safety, radiation, chemicals, stress, and personal history factors. In addition, objective data, including a wide array of medical laboratory tests are assessed. Answers to the survey questions are then evaluated by providing a value to each answer. Healthy lifestyle answers merit a positive, or in some cases a zero value, while unhealthy or risky behavior merit negative scores. Questions are then analyzed based upon the positive/negative scoring and an insurability value is calculated.

These and other objects, advantages and novel features of the present invention will become more apparent from the following detailed description of the invention when considered in conjunction with the accompanying drawings and claims.

BRIEF DESCRIPTION OF THE INVENTION

A. The Hardware and Database

Figure 1:
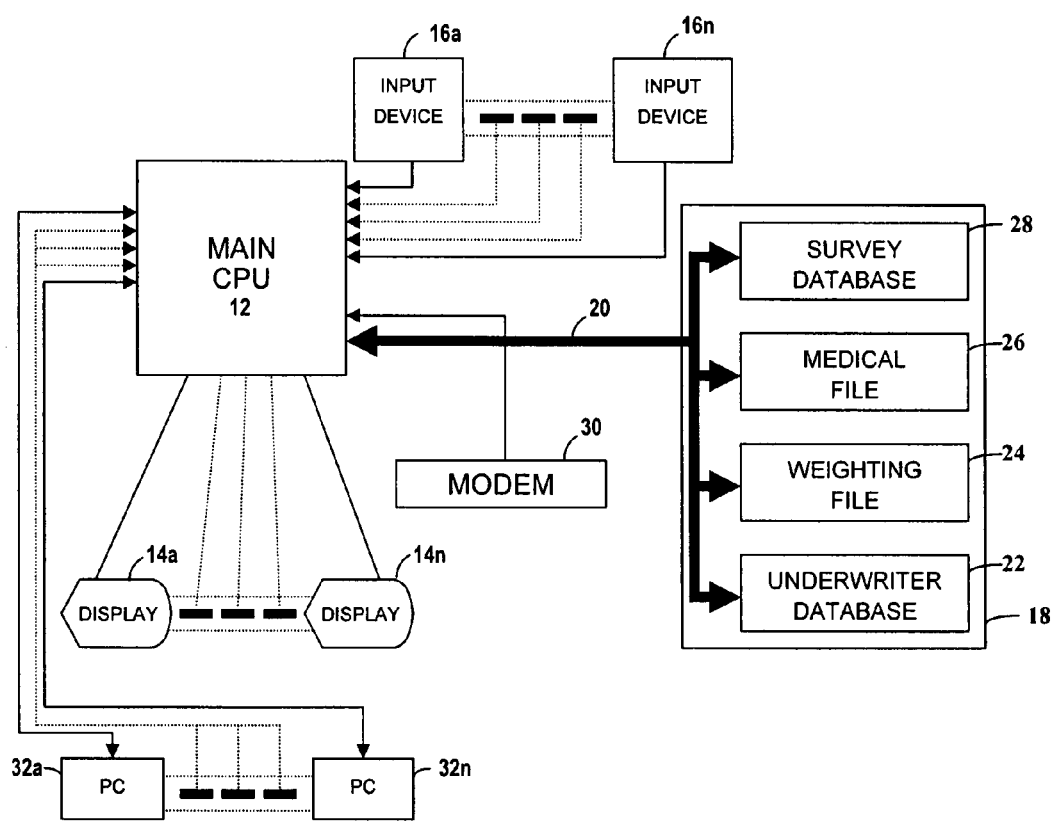
FIG. 1 is a block diagram of a computer system for implementing the present invention.

Referring now to the drawings wherein like reference numerals illustrate like features throughout, FIG. 1 illustrates a general block diagram of a computer system for use in the invention. The system can be implemented in a variety of hardware structures. Preferably, the invention can be realized in an IBM-PC-compatible computer. Alternatively, the invention can be arranged in a minicomputer, or a mainframe computer or in a network of computers, each independently adapted to execute the program. The system, as shown in FIG. 1, is adapted for use on a network and includes a plurality of input devices 16*a*-16*n* which are respectively connected to a main central processing unit (CPU) 12, a plurality of display devices 14*a*-14*n*, and a memory 18. The input devices 16*a*-16*n* and display devices 14*a*-14*n* can be represented as separate PC's connected together by a network (not shown) to the PC, represented by CPU 12.

The memory 18 can be arranged in a number of ways: as a database consisting of a variety of files 22, 24, 26 and 28, as a single file, or as several separate memory devices, each consisting of a single file. For purposes of simplifying subsequent description, it is assumed that memory 18 is arranged as a database having the separate files 22, 24, 26 and 28 shown in FIG. 1, which are arranged to be part of the same PC that includes CPU 12.

The survey database 28 contains answers to questions from a user survey questionnaire. The medical file 26 includes medical data on each particular respondent, organized by respondent name, and provided from the respondent's doctor, medical laboratory, or other pertinent source. The weighting file 24 contains information which relates to numerical weights for answers to survey questions. The underwriter database 22 consists of health insurance underwriting information that provides the employer, insurance underwriter or other interested party, using the weighting data from the weighting file 24, the ability to develop a cost basis for insurability.

The memory 18 is connected through the bus 20 to the main CPU 12. The memory can be located either within the main CPU 12 or can be, for example, located at a remote location and accessed through another CPU. A modem 30 can be used as a connection between the memory 18 and the main CPU 12. In addition, numerous other devices may access modem 30 to provide information to the memory 18. For example, electronically transferred medical data from doctors' offices, or electronic medical databases from laboratories, or information from government agencies (e.g. state public health offices, military, immigration, etc.) may be received in the memory 18 through the modem 30 after connection to an outside electronic database. The main CPU 12 may also serve as an information communicating medium. It can be connected to a network of other similarly used CPU's and/or can receive data from and provide output toga plurality of personal computers 32a-32n. The personal computers 32a-32n may be used in conjunction with, or as an alternative to, the data input devices 16a-16n and display devices 14a-14n.

As noted above, many different types of equipment or computers are suitable for use in the present invention. For example, the main CPU 12 can consist of an IBM-compatible personal computer. If it is used in conjunction with a network of personal computers 32a, then the device can be a relatively powerful personal computer, such as one supplied with an Intel 486 microprocessor. The input devices 16a-16n, in turn, can comprise standard IBM-compatible keyboards, hard drives, optical disks, card readers, tape devices, or other data entry peripherals. Examples of suitable equipment include, but are not limited to, scanners and punch card readers. The display devices 14a-14n can consist of cathode ray tube displays, active matrix displays, liquid crystal displays or the like, that are employed as monitors connected to the main CPU 12. The operations of the FIG. 1 system, and the loading of the memory 18 database will now be described below with reference to FIGS. 2-8 which show, in chart form, the processing executed by CPU 12.

B. System Initialization and Messaging

Figure 2:
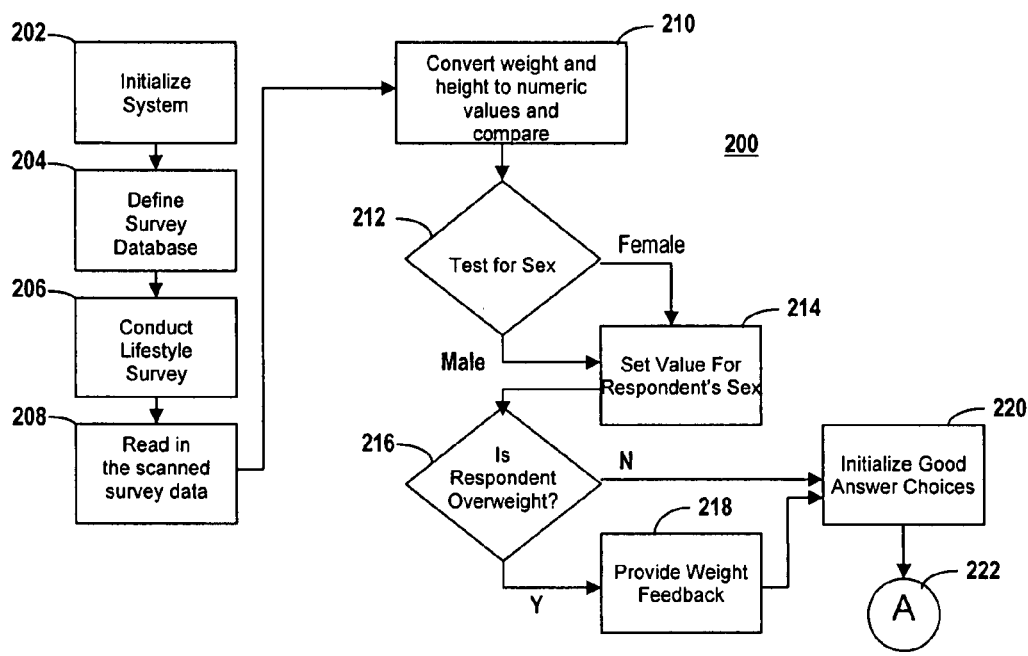
FIG. 2 is a flowchart diagram which illustrates the computer system initialization steps.
Figure 3:
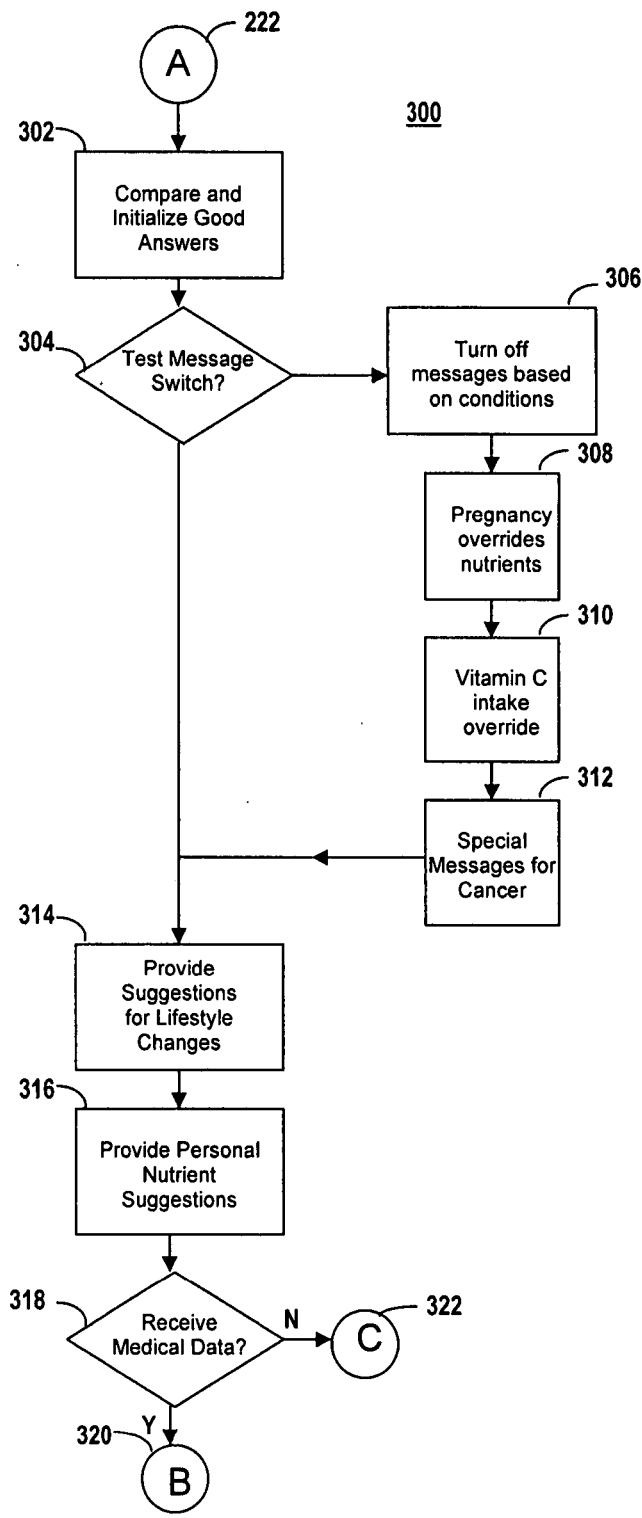
FIG. 3 is a flowchart diagram which illustrates the message test, override and output steps performed by the computer system.

Referring to FIG. 2, an initialization routine 200 is illustrated. The computer system is initialized beginning at step 202. The system initialization includes defining messages that are going to be employed based upon a particular answer to the survey. Those messages will be directed to providing the user with specific health and lifestyle information so the user may in turn use that information to improve his or her personal health and reduce their medical insurance premiums. The purpose of the messages is to therefore provide an incentive for users to modify their risk factors. The messages provide a wide array of information. For example, messages include information pertaining to correct vitamin doses. Based upon a user's answer, the system of the present invention might conclude that vitamin E is low or nonexistent. The computer system would then suggest a different dosage level and also describe the medical importance of vitamin E. The computer system also would recommend the proper manner of vitamin E intake in order to maximize absorption by the body. The computer system may suggest in a message that the intake of certain foods be restricted or might suggest that other foods, or vitamins, are beneficial and their intake should be increased.

The computer system also produces messages that relate to the user's environment, health and nutrition. Individuals providing information on their lifestyle, for example, may receive messages that suggest ways for them to make modifications. For those individuals who spend a lot of time at the beach, for example, the system will produce a message that provides cautionary information on radiation exposure. For those individuals whose diets are excessively heavy with meat, fat or dairy, etc., the system will produce messages on changing dietary habits. Health messages will also include: information for those who smoke or are indirectly exposed to tobacco smoke, information relating to diseases or allergies, information relating to home or work-related risks/exposures, recommendations for exercise, family medical history, the environment, a respondent's weight and height, safety, and recommendations made in response medical test data. The weight and height messages are defined by converting height and weight to numeric values. Specifically, the height is first converted to inches. The weight is then checked in comparison to the height. For males, the weight message is generated by comparison of the person's reported weight to a standard for their height. The standard for males is equal to 110+5(height−60)+10. For females the value is 100+5(inches−60)+10. If the reported weight exceeds the values, the message indicates that the person is overweight.

As part of the initialization routine, the survey database is also loaded in Step 204 into the CPU. In particular, each survey question is associated with a set of potential answers. Each answer has an assigned variable representing values for the answer. Thus, in effect, the data variable will structurally reflect the number of choices for a given question. For example, the variable "P" (person) will include the elements: (1) sex, (2) age, (3) marriage, (4) number of children, and (5) retired. Thus, the person variable will define an array consisting of five elements. The placement of each variable on the menu is also initialized at this stage.

At Step 206, the questionnaire survey is initiated. The survey is designed so that it can be asked by way of a display device on the PC and answering interactively at an input device on a computer keyboard or by way of other input devices. The survey is designed to provide a group of questions which test the user's health and lifestyle. The questions range from a plurality of categories including: (1) personal information, (2) geography, (3) occupation, (4) present nutrition, (5) past nutrition, (6) height and weight, (7) tobacco use, (8) alcohol use, (9) hormonal factors, (10) exercise, (11) stress, (12) radiation and chemicals, (13) personal history, (14) drug use, (15) family history, (16) safety, (17) medical information, and (18) pets. Furthermore, a separate medical information questionnaire is also sent to an individual's doctor or lab technologist. That questionnaire seeks information on cholesterol, triglycerides, glucose, liver functions, urine information, blood pressure and the respondent's weight and other medical information.

At step 208, the answers from the respondent are input into an input device of the computer system, as shown in FIG. 1. The manner of input is varied. For example, the answers can be supplied by the keyboard, as discussed, or read in from punched data cards, read in from a magnetic tape, communicated by modem, or converted from audio data, such as from a telephone voice messaging system. Once read in, the data are then pre-processed to initialize variables and to also provide initial measurements for later processing. At step 210, the user's height and weight data are converted to numeric values and are compared to scale values. The compared amount is used as a basis for judging whether or not the respondent is overweight.

At step 212, the sex of the respondent is tested, and the variable representing sex is set at step 214. Steps 216-218 then provide the user's weight analysis, using height, weight and sex as the variables. If appropriate, an overweight message is then provided to the respondent at step 218.

Messages can be provided in numerous ways. If the respondent is located at a computer terminal, messages can be flashed across the screen of a display device. Additionally, security software can be employed to assure the privacy of the message. Messages may also be printed, or provided by a suitable voice messaging system. Any suitable output device, however, is contemplated for retrieving messages to a user.

At Steps 220 and 302 good answer values are initialized for each variable. In other words, each answer is defined with respect to the value it will have on the weighting data when a health insurance premium level and amount are defined. Once the values are initialized, then the actual answers to the scanned survey are tested in Step 304. The first answers to be defined are those that actually control other messages based upon a user's particular conditions 306. One condition that effects on particular messages is pregnancy 308. A pregnant individual will receive messages pertaining to nutrients. Specifically, if the user is pregnant, the computer system overrides nutrient data. The respondent is then advised to consult with her doctor about nutrition. The system then automatically checks for all other possible nutrient overrides and provides holds on certain nutrients which should still be messaged to the pregnant user. For example, it is well known that a pregnant woman needs to retain high beta-carotene nutrients and high vitamin E levels. At step 310, the calcium intake override is also tested. This is a message override which is designed to provide vitamin C level advice dependent upon user provided responses. Hence, the system provides information to the respondent on high, medium and low levels of vitamin C intake and provides appropriate output messages. Other overrides are for low fat, high fiber diets and special messages pertaining to cancer and heart disease (step 312).

Once the special messages are complete, then the messages for nutrient modification, personal history or health/ lifestyle risks are provided. Each message is first initialized and the suggested lifestyle modifications are then printed out, displayed or output to the user in any suitable manner. Once the lifestyle suggestions are provided at step 314, according to the messages discussed previously, then a nutrient suggestion is displayed at Step 316. Personal nutrient suggestions are tailored to user responses. Finally, a personal history group of answers will be printed or displayed at step 318. Prior to messaging, the database 26 is tested to see if a medical file for the respondent was developed. If such data exists, then the data is retrieved by causing computer processing to jump at Step 320. If no data has been received, the system then goes directly to a personalized lifestyle analysis (FIG. 5) which will be described in further detail below.

Figure 4:
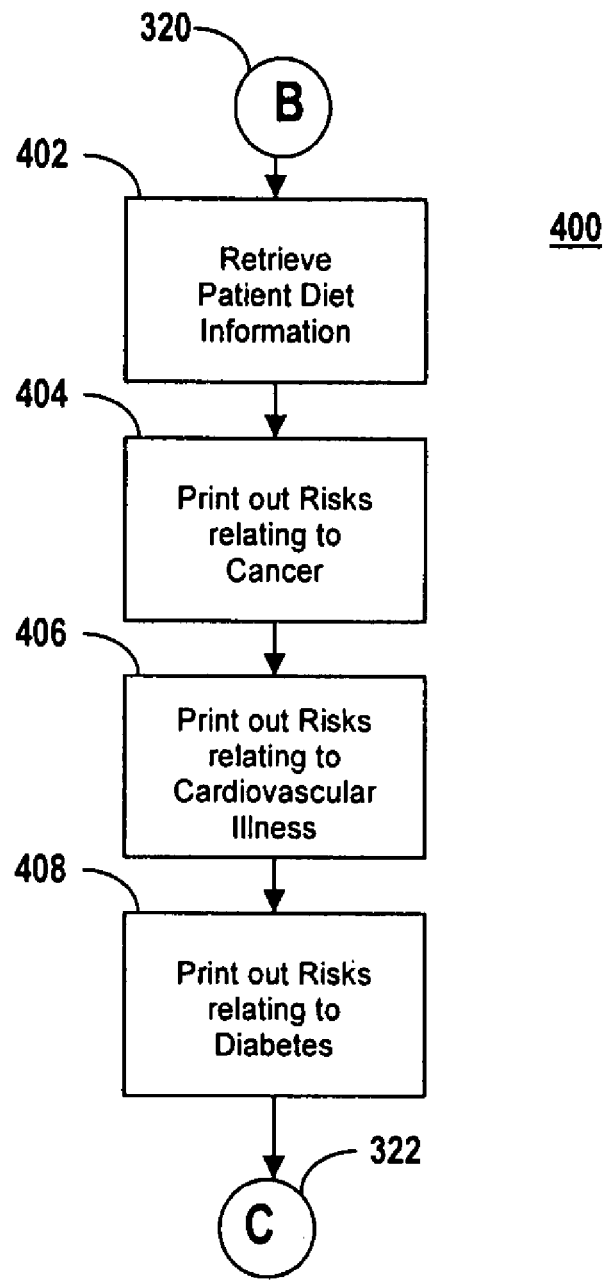
FIG. 4 is a flowchart diagram which illustrates the steps for retrieving and communicating medical test data.

Referring now to FIG. 4, personal history selections begin by retrieving patient diet information at Step 402. Once the medical data is tested in conjunction with the diet information, an assessment of the individual's risks relating to a variety of diseases, such as cancer 404, cardiovascular illness 406 and diabetes 408, are assessed and messages provided. Upon completion of the analysis, processing proceeds to initiating the personalized lifestyle analysis at Step 322.

C. Personal Lifestyle Analysis

Figure 5:
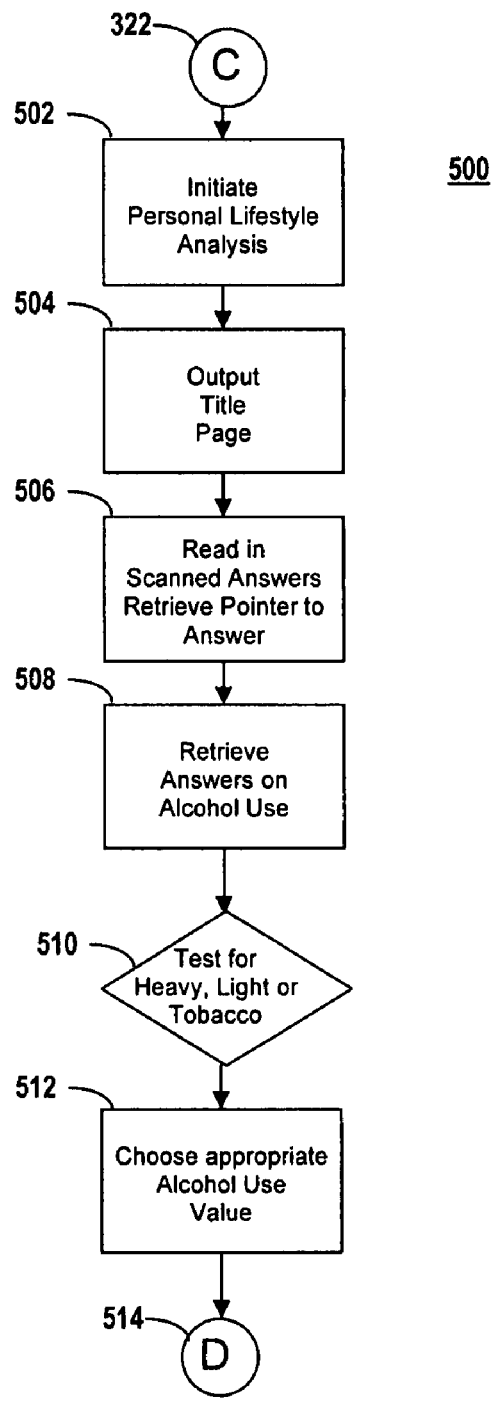
FIG. 5 is a flowchart diagram which illustrates the steps for the personalized lifestyle analysis.

Referring now to FIG. 5, the personalized lifestyle analysis 500 is initiated by first reading in background data including a respondent's address, city, date, and time. Answers from the survey are then read in and an output title page 504 is subsequently produced. The system then passes answer data structure pointers to the personalized data routine. The pointer provides an address located in the survey database 28 and the medical file database 26 for the individual respondent.

The retrieved answers are then compared to the list of "good" answers stored in the answer database 28. An appropriate switch message structure is then set based upon the quality of the answer. The message switch usually determines which message will be printed at step 506. The final initialization step includes removing all trailing blanks from the strings of data passed to the computer system. A modified string is returned to the database. If the retrieved string is entirely blank, the initialization function returns a null string.

The first answers to be retrieved and analyzed relate to alcohol use. At Step 508, alcohol answers are generated from an evaluation of the questionnaire. In particular, the answers are compared to preset levels to define whether alcohol use is high, low or medium. In addition, answers pertaining to whether alcohol is used in conjunction with tobacco is also tested. An appropriate value is then provided to the answer array at Step 512.

Figure 6:
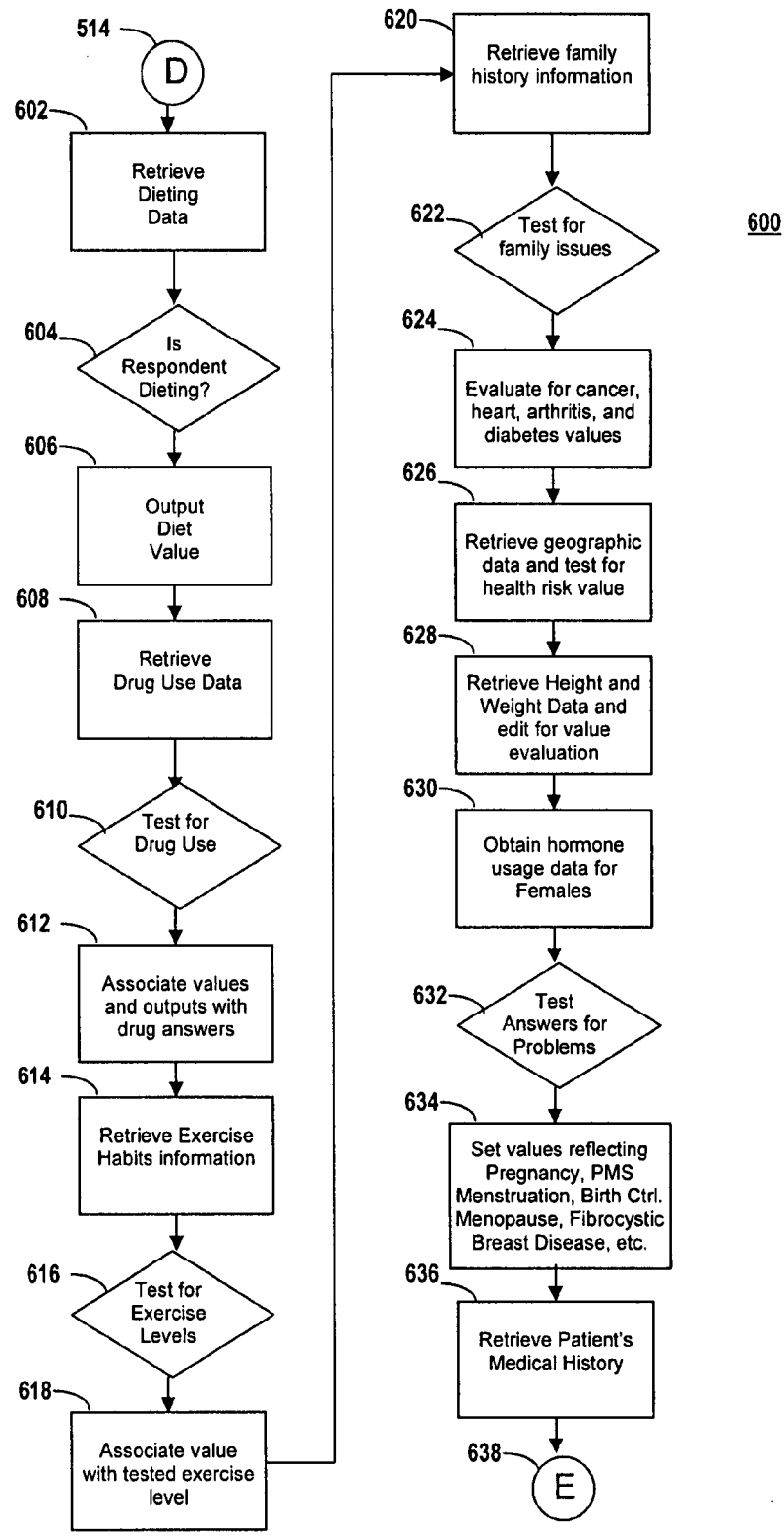
FIG. 6 is a flowchart diagram which is a continuation of the diagram shown in FIG. 5.
Figure 7:
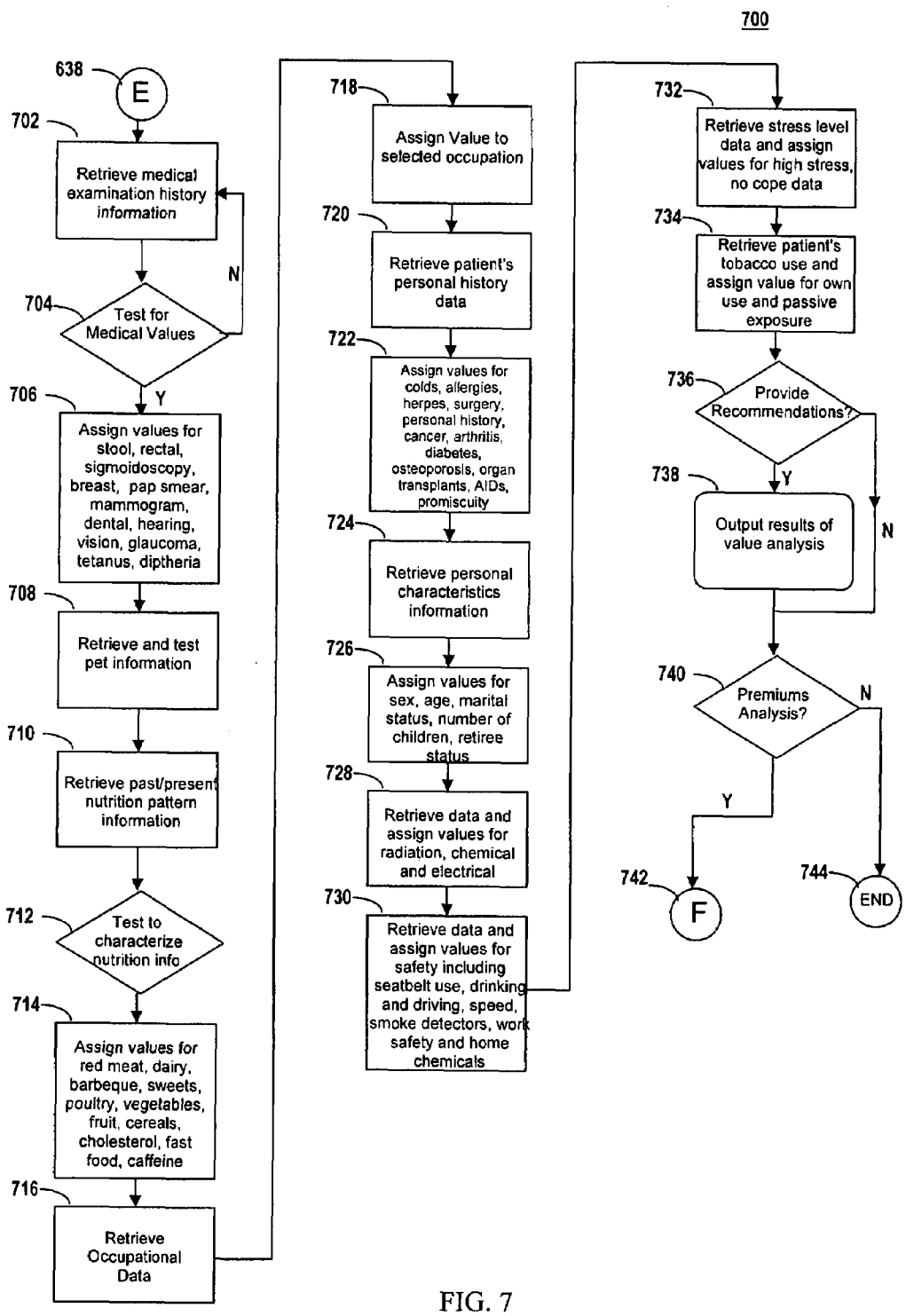
FIG. 7 is a flowchart diagram which is a continuation of the diagram shown in FIG. 6.

Referring now to FIG. 6, details regarding the personalized lifestyle analysis processing steps are shown. At Step 602, the system is tested to see if the patient is dieting to lose weight. If the user indicates that he or she is dieting, then an output value is provided relating to the diet at Step 606. Steps 608 through 612 test for drug use and, in particular, for answers pertaining to the use of the drugs crack, cocaine, tetracycline, birth control pills, deconvulsents, diuretics, hydralazine, colchicine, INH/PAS or trimethoprim. The user is also tested for laxative use and steroids (chlorambucil, cyclophosphamimide, melphalan or high-dose steroids (anti-cancer drugs)). Appropriate values and messages are then assigned to these answers at Steps 612.

The user then is tested for exercise habits at Step 614. Questions regarding exercise include: (1) the type of exercise the user performs, (2) the number of times per week that the exercise occurs and (3) whether or not the user warms up or cools down. Values are assigned to the exercise answers at Steps 616 and 618.

The survey also evaluates family history and, in particular, genetic preponderance for cancer and other diseases. Those diseases include heart disease, stroke, and hypertension. Proclivity for arthritis as well as diabetes are also tested and values are associated with the information at Steps 622 and 624. At Step 626, geographic information is analyzed. In particular, the user answers two questions: does he or she spend the majority of his or her time in the city or suburb and what region of the United States does he or she live in. The geographic data is tested and messages are provided pertaining to health risks at Step 626. For example, individuals living in the city or suburbs will be provided with air pollution messages and those living in certain regions of the country may be given data pertaining to cancer risk. At Step 628 the individual's height and weight data are retrieved. Values are then assigned to that data based upon the conversion and calculations made during system initialization (see FIG. 2). Weight messages are then provided to the user and a value is associated with that individual's health.

At Step 630 hormone usage information is analyzed. However, prior to analysis, the message switch is tested to determine whether the individual is pregnant or is breast feeding. Other hormonal information is also checked including whether the respondent is presently menstruating, having pre-menstrual syndrome, menopausal, using birth control pills, having lumps or fibrocystic breast disease, or having an early or late onset of menses, menopause, or never having menses at all. Also, the respondent is questioned whether they are pregnant late in life, or never at all. Answers and values for the hormonal information will then be reflected in both the insurability determination and in the automated messaging pertaining to the health-related suggestions. Additionally, common sense suggestions concerning hormonal issues are provided to the user.

At Step 636 the patient's medical history is then retrieved. As previously explained, medical information comes from two sources: from the patient's own response to the medical examination questionnaire, and from the lab technician. With respect to the questionnaire, the user is asked twelve questions. Those questions concern general "yes" or "no" answers relating to the user's medical exam history. The user is first asked whether or not they had a comprehensive physical exam and whether or not they have had a stool test for hidden blood. Other questions include whether the respondent had a rectal exam, a colonoscopy or a sigmoidoscopy. The user is further asked if he or she had a breast exam, a pap smear, a baseline mammogram (for ages 35 to 50), yearly mammograms (for ages greater than 50), dental exams, hearing tests, vision tests or glaucoma tests within the past ten years. Each of the medical exam questions is then answered and a value is assigned. Messages are also provided to the respondent about what those tests show and the value and significance of those tests. For those individuals answering negatively to the survey, messages suggesting medical examinations are provided. At Step 708, the user's answers pertaining to pets is retrieved. Two questions are asked: does a respondent have a cat or a dog. Values are accordingly assigned to that information at Step 708.

Upon completion of the survey, a detailed analysis of past nutrition patterns is performed. This information is provided in the questionnaire, which indicates nutrition patterns during the last 50% (or more) of the respondent's life. Information tested includes quantities of red meat eaten per week, quantities of eggs eaten per week, quantities of butter, milk or cheese daily, quantities of fiber taken daily, the frequency of barbecued food and the average intake of vitamins and minerals. Data to these questions are then analyzed for the nutritional "health" of the individual. Numerical amounts are then assigned to the various foods intake levels.

Occupational data is then retrieved and tested. The occupational information retrieved by the computer system includes determining the industry an individual works in. Four categories are defined: a homemaker, a worker in a high-risk industry (petroleum, dyes, rubber, fungicides, painting, chemists, pharmaceuticals, etc.), a professional worker or worker in a low-level, moderate exposure workplace, e.g. transport equipment service worker. Once the value for the selected occupation is assigned and an appropriate message given in Step 718, the patient's personal history data is then retrieved. The personal history relates particularly to medical history. It asks respondents about their minor ailments, such as colds, allergies, herpes, asthma, as well as serious ailments, such as heart disease, cancer, arthritis, diabetes, osteoporosis, immune deficiencies, and AIDS.

Lifestyle questions in an individual's personal history include social/sexual behavior questions (e.g. Have you had sexual encounters before age 16? Have you had many partners?, etc.). At Step 724 personal characteristic information is also retrieved and weighed. That information reflects the individual's age, sex, marital status, number of children and retiree status. An individual's radiation and chemical exposures are then tested at Step 728 and data and values are assigned at Step 730. The tested data include information pertaining to sunburn, the quantity of radiation exposure (x-rays, radiation treatments, radioactive isotopes), and electric magnetic field exposure. A group of dangerous chemicals are also listed and the respondent is asked to indicate whether or not he or she works with them. As an example, those chemicals may include aniline, acrylonitrile, 4-aminobiphenyl, arsensic, asbestos, auramine, benzene, benzidene, beryllium, cadmium, carbon tetrachloride, chlormethyl ether, chloroprene, chromate, isopropyl, alcohol, nickel, mustard gas or vinyl chloride. Finally, the respondent is asked if he or she works indirectly with the above-identified chemicals. A risk value is then assigned at Step 730.

The user is then tested at Step 732 for stress. The respondent is asked whether he or she is either overworked or has a stressful or difficult life, a recent loss of a loved one or problems with sleep. A question is also directed to whether the user is unable to cope with stress. Finally, the user is questioned concerning tobacco use and second-hand tobacco exposure. Recommendation messages are provided at Step 734.

At Step 736 the user is asked if he or she wants to print out the answers or exit the session. If the answer is yes, the output results of the value analysis are printed. Otherwise an exit automatically occurs. Premiums analysis of the program is then queried at 740. If the user answers yes, the routine at Step 742 jumps to the routine identified in FIG. 8. Otherwise, processing ends at Step 744.

D. Premium Evaluation and Analysis

Figure 8:
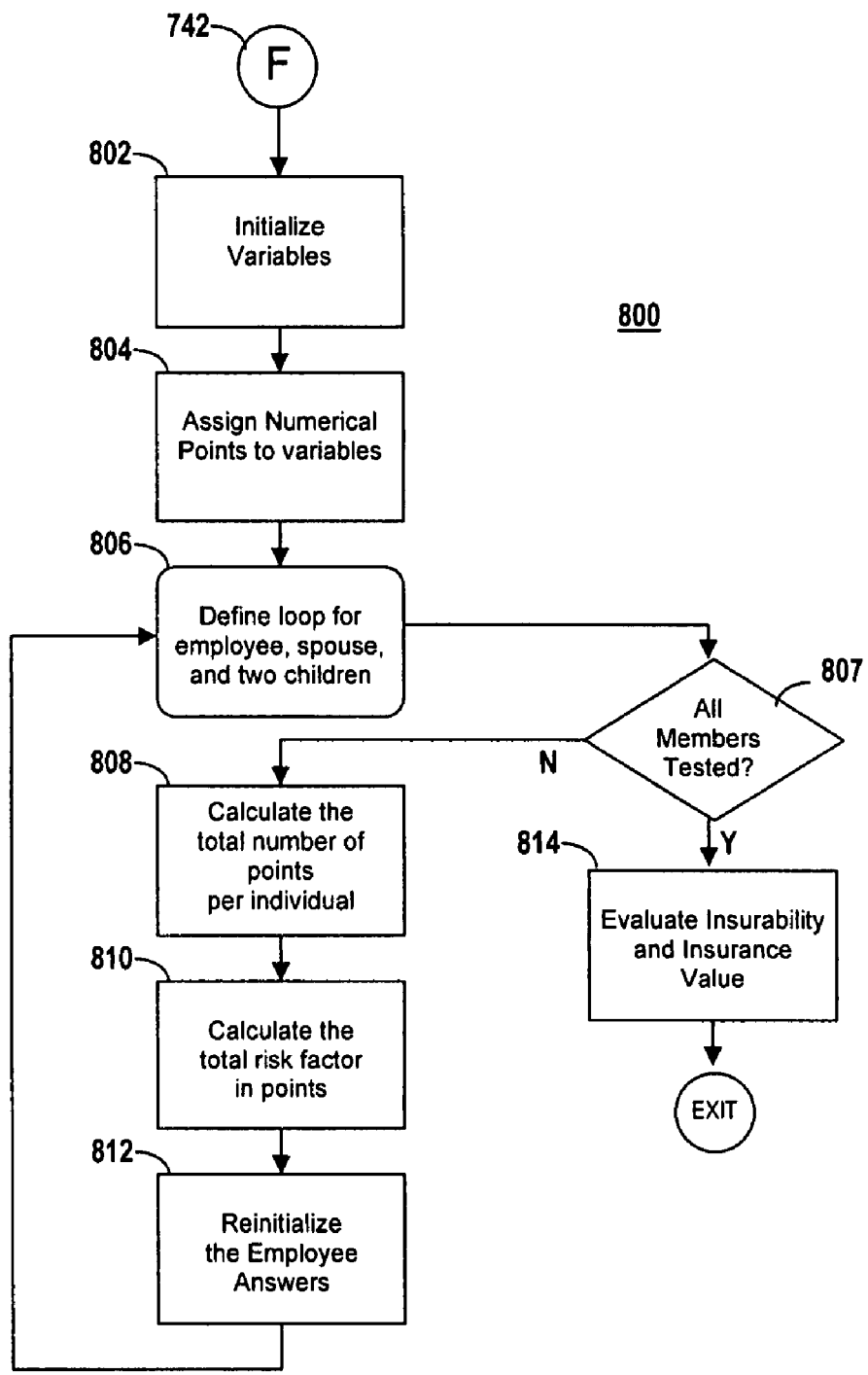
FIG. 8 is a flowchart diagram which is a continuation of the diagram shown in FIG. 7.

Referring now to FIG. 8, the analysis for evaluating a medical insurance premium data is entered. Before discussing the details of this routine, it should be noted that, although the invention is discussed in terms of its applicability to evaluation and underwriting health insurance, the invention can also be applied to other applications. For example, the present invention can also be employed for evaluating life insurance, property insurance, automobile insurance, or other casualty-related insurance policies. Moreover, the present invention need not be restricted to the insurance industry. The weighting and evaluation of medical, data may be pertinent to other fields, such as in personnel decisions, military fitness, or for medical applications.

At Step 802 the variables are initialized. These variables pertain to the weighting database and are refined with weight level limits based upon the values assigned in the survey database. Once the variables are initialized, then a numerical weight is assigned to each value at Step 804. Weights, in the present invention, are positive and negative values which are used as multipliers for defining health insurance premium values. Each weight's value depends upon the assessed medical risk for a given category. For example, a positive response to the question "Do you smoke" will be weighted heavily negative, while a positive response to the question "Do you eat red meat twice a week" will only receive a slightly negative score. Weighting calculations can be more complex and can incorporate risk factors that are unique to the respondent. For example, if the respondent provides information indicating a family history of heart disease, then the slightly negative value for red meat consumption may be increased to reflect a mid-level negative risk value. The assigned weights are defined by a medical insurance specialist, a doctor, and nutritionist or others using known mortality statistical data and other underwriting information. That information can be pre-stored in the underwriter database 22 and associated with particular questions contained in the survey database 28 and the weighting file 24.

At Step 806, a processing loop is initiated for each employee along with his or her spouse and up to two children. Obviously, the loop can be modified for any family size covered under one policy. The loop is then tested at Step 807 to see if it has evaluated all members on the policy and has evaluated all questions in the survey. If the processing loop is not complete, then at Step 808 the answer to each question for each individual in the survey is assessed for a numerical value. Although many schemes exist for associating numerical values with survey answers, in the preferred embodiment a positive response is given a value of "1" while a negative response is valued at "0". Once the values are assigned to each answer, then the previously described weights assigned to the particular respondent and to the particular answer are used to multiply the answer value for a total risk factor amount at Step 810. The calculation occurs as follows.

First the survey database 28 is accessed by the CPU 12 to see how the respondent answered the particular survey question being tested by the loop. If, for example, the question "red meat, twice a week" is being processed in the loop for the father of the family, and his answer is "yes", then a value of "1" is retrieved from database 28. The weighting file 24 for the red meat question is then accessed by CPU 12. The calculated weight for the father is then assessed. This is done by first retrieving a base weight value from the weighting file 24. For example, that value is (−100). Various databases are then queried for other factors that the weighting information directs the CPU 12 to inquire about. In this example, the weighting file for the red meat question indicates that a high family history value for heart disease would affect the weight calculation by adding a negative twenty points to the weight. Accordingly, the CPU 12 retrieves from the survey database 28, the father's response from the family history question about heart disease. In this instance it indicates a high incidence in his family of heart disease (a score of "1"). As a result, a value of (−20) would be assigned. The weight file 24 also indicates that several other factors need to be evaluated to affect the weight. First, the father's weight needs to be assessed. The CPU is then directed to access the survey database 28 for this data. Since the father is ten pounds overweight, he is assigned an additional score of −10 by the CPU 12. A final factor indicated by the weighting file 24 is blood cholesterol. As a result, the CPU 12 checks the father's medical file 26 to determine his cholesterol level. Since his level is deemed moderately high according to categories in the medical file, then a further negative weight value of, for example, −10 is assigned. The overall weighting for the answer is thereby evaluated as −140.

To determine the risk, the answer value and weight are multiplied (1×−140) and a risk value of −140 is assigned to the father's score for the survey. The value is then loaded into the underwriter database 22 to be used to provide evaluation of the insurance costs for the father.

The underwriter database 22 and subsequent analysis performed at step 814 are directed to assigning categories and/or monetary values to policyholder scores once all questions in the survey have been assigned a risk value at step 810. The analysis takes place at step 814. Where an entire family constitutes one policy, then their total risk scores for the survey are averaged. However, other evaluation techniques commonly used in the health insurance underwriting business can be employed to evaluate and score risk for a family. Categorization can also occur in the underwriting analysis. For example, the present invention contemplates a system where four levels of insurability and associated cost are attributed to particular scores. The first level, dependent on the number of accumulated negative and positive points calculated at Step 810, is for a policyholder with an overall positive "score" from the survey. The second level would include scores from zero to a small negative (i.e. −500). This second level would indicate individuals who have a moderately healthy lifestyle, but who may need to make relatively minor adjustments to receive a better health insurance premium. The third level would be for individuals who score in the medium negative range (i.e. −501 to −1000). These individuals may represent higher risks to the insurer or company, and may result in the policy holder having to pay considerably more for health insurance. Finally, the fourth category would include high negative scores (greater than −1001). Those individuals may risk very high insurance rates or may be denied coverage altogether.

Returning to FIG. 8, once a risk amount is calculated for each individual, the weight and value data are re-initialized. Once the risk valuation loop is complete for all survey answers for all policy members, then the afore-mentioned insurability analysis occurs at step 814 producing a health insurance premium value.

As a result of the analysis, companies, individuals and insurers will have an opportunity to more fully and rapidly assess the cost and insurability of an individual, while at the same time, automatically assess and communicate lifestyle modifications for the respondent. As a consequence, the system presents an efficient, automatic and easily implemented solution to predict health care costs, and to stem the potential for increased costs and risks to the employer and health risks to the employee.

From the preceding description it is evident that the invention has been described in detail by reference to a particular embodiment adapted for use in the field of health insurance. Although this invention does offer some advantages, it may be used in other fields advantageously as well. Accordingly, this invention is not intended to be limited by the details of the preferred embodiment described above, but rather by the terms of the appended claims.

We claim:

1. A computer system for evaluating insurability of at least one individual, comprising:
  a display means for displaying a plurality of survey questions pertaining to said individual's lifestyle, health, and medical tests;
  entry means for inputting information into said computer system in response to said plurality of survey questions and for causing said display unit to display said information;
  a computer system database for receiving and storing said information;
  means for verifying whether at least some of said information is true by comparing said information with additional information;
  means for deleting, adding to, or changing said information subsequent to having received and stored said information;

means for assigning weight values in a weighting file in said computer system database, said weight values being assigned by analyzing said information;

means for assigning risk values to each of said weight values that represent levels insurance risk;

means for determining a total value based upon said assigned risk values and said assigned weight values for all of said information;

choosing means for selecting certain information and certain pre-defined suggestions on medical and lifestyle choices that would lead to improving health and decreasing risk and that have similar subject matter to said information;

evaluating means for comparing each of said total values for said information with pre-defined accepted values and for comparing said chosen pre-defined suggestions with said information, wherein pre-defined suggestions are selected that are specific and closely-tailored to said information and to the needs of said individual, including recommendations for treatment of health problems and for altering lifestyle to ensure better future health;

messaging means for providing messages that contain said pre-defined suggestions;

analyzing means for determining said level of insurance risk such that both a cot and an insurability profile are determined; and communicating means for automatically communicating said level of insurance risk.

2. The computer system for evaluating insurability of claim 1, wherein said means for assigning risk values assigns negative values for actions that increase insurance risk and positive values for actions that decrease insurance risk.

3. The computer system for evaluating insurability of claim 1, further comprising a second database to store underwriter information including said risk values and said weight values.

4. The computer system for evaluating insurability of claim 1, further comprising a questionnaire database means to store a questionnaire said questionnaire being employed by said survey means in order that such individual can select appropriate responses to lifestyle question.

5. The computer system for evaluating insurability of claim 1, wherein said pre-defined suggestions are automatically differentiated by said computer system for pregnant users.

6. The computer system for evaluating insurability of claim 1, wherein said information about lifestyle includes tobacco use, alcohol use and food intake.

7. A method of evaluating in a computer system insurability of at least one individual, comprising the steps of:

inputting information pertaining to lifestyle, health, and medical tests into said computer system;

receiving and storing said information in a database in said computer system;

deleting, adding to, or changing said information subsequent to having received and stored said information;

verifying whether at least some of said information is true by comparing said information with additional information acquired from a third party;

assigning weight values by said computer system for each of said stored information, said weight values being assigned by analyzing said information;

assigning of risk values by said computer system to each of said weight values that represent levels of insurance risk;

said computer system determining a total value based upon said assigned risk values and said assigned weight values for all of said information for such individual;

creating an insurance comparison by said computer system comparing each of said total values for said information with pre-defined accepted values stored in said database of said computer system;

choosing certain information and certain pre-defined suggestions on medical lifestyle choices that would lead to improving health and decreasing risk and that have similar subject matter to said information;

comparing said chosen pre-defined suggestions with said information wherein pre-defined suggestions are selected that are specific and closely-tailored to said information and to the needs of said individual, including recommendations for treatment of health problems and for altering lifestyle to ensure better future health;

providing messages from said computer system that contain said pre-defined suggestions;

determining through said computer system said level of insurance risk such that both a cost and an insurability profile for each of such individuals is determined; and automatically communicating said level of insurance risk.

8. The method of evaluating insurability of at least one individual in claim 7, wherein said step of inputting information comprises the steps of:

providing said individual with a questionnaire through said computer system, said questionnaire in the form of a plurality of survey questions; and receiving said individuals answers from said questionnaire into said computer system.

9. A computer system for evaluating insurability of at least one individual, comprising:

a display unit for displaying a plurality of survey questions pertaining to said individuals' lifestyle, heath, and medical tests;

an entry unit for controlling said display unit and for inputting information in response to said plurality of survey questions displayed on said display unit;

a computer system database for receiving and storing said information;

means for deleting, adding to, or changing said information subsequent to having received and stored said information;

a verifier for verifying whether at least some of said information is true by comparing said information with additional information provided by a third party;

a weight analyzer for assigning weight values in a weighting file in said computer system database, said weight values being assigned by analyzing said information;

a risk assignor for assigning risk values to each of said weight values that represent level of insurance risk;

a summing unit for determining a total value based upon said assigned risk values and said assigned weight values for all of said information;

a selector for selecting certain information and certain pre-defined suggestions on medical and lifestyle choices that would lead to improving health and decreasing risk and that have similar subject matter to said information;

a comparator for comparing each of said total values for said information with pre-defined accepted values and for comparing said chosen pre-defined suggestions with said information, wherein pre-defined suggestions are selected that are specific and closely-tailored to said information and to the needs of said individual, including recommendations for treatment of health problems and for altering lifestyle to ensure better future health;

a messaging unit for providing messages that contain pre-defined suggestions;

a risk analyzer means for determining said level of insurance risk such that both a cost and an insurability profile is determined; and a communication unit for automatically communicating said level of insurance risk.

* * * * *